(12) United States Patent  
Dannecker et al.

(10) Patent No.: US 6,691,946 B2
(45) Date of Patent: Feb. 17, 2004

(54) MEDICAL BOWL FOR COILED DEVICES

(75) Inventors: Bruce Dannecker, Tyler, TX (US); Doug Cundieff, Jacksonville, TX (US); John Holland, Tyler, TX (US)

(73) Assignee: Allegiance Corporation, McGaw Park, IL (US)

( * ) Notice: Subject to any disclaimer, the term of this patent is extended or adjusted under 35 U.S.C. 154(b) by 0 days.

(21) Appl. No.: 10/062,692

(22) Filed: Jan. 30, 2002

(65) Prior Publication Data

US 2003/0141407 A1 Jul. 31, 2003

(51) Int. Cl.⁷ .......................... B65H 75/16; B65H 85/02
(52) U.S. Cl. ................... 242/588.6; 242/400.1
(58) Field of Search ............... 242/588.6, 588.3, 242/400.1, 405.1, 405.2, 141, 146, 137, 137.1, 138, 132, 129; 206/438, 388, 459.5, 408, 389, 515, 519, 520, 505; 215/365, 366; 604/171

(56) References Cited

U.S. PATENT DOCUMENTS

| 4,226,328 A | * 10/1980 | Beddow .................. 206/364 |
| 4,282,972 A | * 8/1981 | Chiulli .................... 206/303 |
| 4,566,606 A | 1/1986 | Kling ....................... 221/25 |
| 4,915,216 A | 4/1990 | Magers ................... 206/520 |
| 4,936,448 A | 6/1990 | Holloway ............... 206/364 |
| D364,564 S | 11/1995 | Moore ....................... D9/429 |
| 5,611,428 A | 3/1997 | Banerian ................ 206/364 |
| 5,738,213 A | 4/1998 | Whiting et al. ....... 206/364 |
| 5,769,222 A | 6/1998 | Banerian ................ 206/364 |
| D433,130 S | 10/2000 | Cude et al. ............ D24/121 |
| 6,237,770 B1 | 5/2001 | Bowsman ............... 206/438 |
| 2002/0157981 A1 | * 10/2002 | Whiting et al. ....... 206/438 |

FOREIGN PATENT DOCUMENTS

WO  WO9856687 A  * 10/1980

* cited by examiner

Primary Examiner—Kathy Matecki
Assistant Examiner—Scott J. Haugland
(74) Attorney, Agent, or Firm—Andrew G. Rozycki

(57) ABSTRACT

The invention described herein relates to a medical bowl adapted to accommodate and retain a coiled medical device comprising: generally smooth cylindrical sidewall portion; a generally planar circular bottom portion; and a plurality of retention tabs extending upward from said bottom portion and positioned thereon to provide a space between said sidewall portion and said retention tabs. The retention tabs are structured and positioned to facilitate the handling and grippability of a coiled device placed within the bowl.

12 Claims, 7 Drawing Sheets

MEDICAL BOWL FOR COILED DEVICES

FIELD OF THE INVENTION

The invention relates to the field of medical devices and equipment useful during medical procedures. In particular, the invention pertains to a bowl for storing and handling medical items, such as catheters and guidewires, that can be placed in a compact coiled configuration.

BACKGROUND OF THE INVENTION

Certain medical devices and equipment by virtue of their structure and materials necessitate a compact coiling thereof in order to facilitate their storage, packaging or handling. Such devices and equipment include items used during various medical procedures include, but are not limited to, guidewires, flexible stents, catheters, tubing, wires, fiberoptic equipment, and the like. These devices can prove awkward to handle and manipulate by virtue of their resistance to compact coiling and tendency to expand outward in a radial direction. Accordingly, controlling the storage and handling during medical procedures of such items is important, since these items can become physical obstacles and have compromised sterility when handled inappropriately.

A variety of guidewire and catheter bowls are currently available in the medical field. One such bowl is described in Magers U.S. Pat. No. 4,915,216, which describes a surgical bowl having inwardly projecting sidewall lugs which maintain a coiled wire at the bottom of the bowl. Another bowl is described in Holloway U.S. Pat. No. 4,936,448, which describes a catheter bowl with integrally molded retaining members on the sidewall of the bowl. Yet another bowl is described in Cude et al. U.S. Pat. No. Des. 433,130, drawn to an ornamental design of a catheter or guidewire bowl containing extended portions protruding from the sidewall and an intermittently raised base. These bowls described in these references, however, are primarily designed to only control the upward migration of a coiled item placed within, and fall short of affording the user optimal ease of handling and grippability of the item while inside the bowl.

None of these references offer the user the advantages associated with separating the coiled item from the side and bottom of a bowl when placed therein. Thus, there is a need for a medical bowl which can accommodate a coiled device in a manner which facilitates the storage and handling of the coiled device and is relatively easy to manufacture.

SUMMARY OF THE INVENTION

The invention provides a medical bowl for coiled devices having an improved design. More particularly, it has been discovered that a medical bowl can possess a structure and position of retention tabs such that the bowl: 1) improves handling and grippability of a coiled device placed within the bowl by providing i) a gap between the sidewall and retention tabs which utilizes the tendency for outward radial expansion of the coiled device to additionally provide ii) a gap between the coiled device and the bottom of the bowl; 2) enhances the separation of the coiled device from resident fluids inside the bowl; 3) can be stored in stackable, space-saving manner when empty or when containing a coiled device within; and 4) can be manufactured using an integrally molded single piece construction. The medical bowl according to the invention is useful for the storing and handling a variety of devices having a coiled configuration, including but not limited to, guidewires, flexible stents, catheters, tubing, wires, fiberoptic equipment, and the like.

The invention provides a medical bowl adapted to accommodate and retain a coiled medical device comprising:
- a generally smooth cylindrical sidewall portion;
- a generally planar circular bottom portion;
- a plurality of retention tabs extending upward from said bottom portion and positioned thereon to provide a space between said sidewall portion and said retention tabs.

In a preferred embodiment, each of the retention tabs comprises:
- an outer side, an inner side, a top portion and a base;
- wherein
- said outer side is upright and generally parallel to said sidewall portion;
- said inner side comprises an incline portion located at the base; and
- said top portion comprises a lip extending inward toward the central region of the bowl.

Additional advantages and aspects of the invention will be apparent from or pointed out in the course of the detailed description of the preferred embodiment which follows.

BRIEF DESCRIPTION OF THE DRAWINGS

The following drawings further illustrate the invention, the drawings not being intended to be construed as limitations as to particular structures or designs.

DETAILED DESCRIPTION OF THE INVENTION

The term "medical bowl" as used herein is meant to include use of the invention with a variety of items which when placed therein can form a coiled configuration, and therefore benefit from the invention. The term is not intended to imply a limitation as to a particular component or component material placed therein, nor is the term intended to preclude contents in addition to items having a coiled configuration. Examples of other items can include, for example, guidewires, flexible stents, catheters, tubing, wires, fiberoptic equipment, and the like.

As used herein, the term "generally smooth" when used in association with the sidewall is meant to refer to the absence of substantially protruding structures extending toward the inside of the bowl. The term is not intended to preclude slightly raised indicia or markings located on the interior surface of the sidewall.

The term "generally circular", when used in association with the bowl bottom, is meant to refer to an overall rounded shape of the bottom portion of the bowl which can correspond to the overall coiled configuration of the intended contents for the bowl. Accordingly, the term is meant to encompass slightly oblong or oval shape as well.

The term "substantially perpendicular" when used in the context of describing the position of the retention tabs is meant to refer to the overall orientation of the tab relative to the bottom portion of the bowl. The term is not meant to preclude various shapes of the tab per se, such as a thicker, inclined portion.

Figure 1:
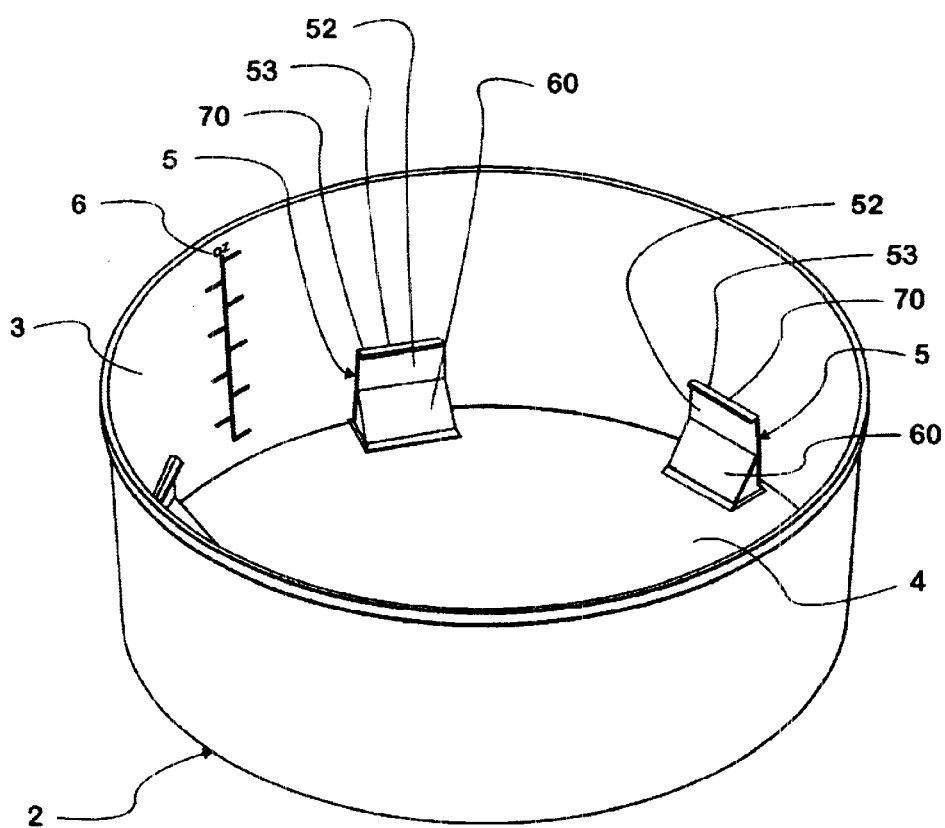
FIG. 1 is an angled side view perspective of the medical bowl according to one embodiment of the invention.
Figure 2:
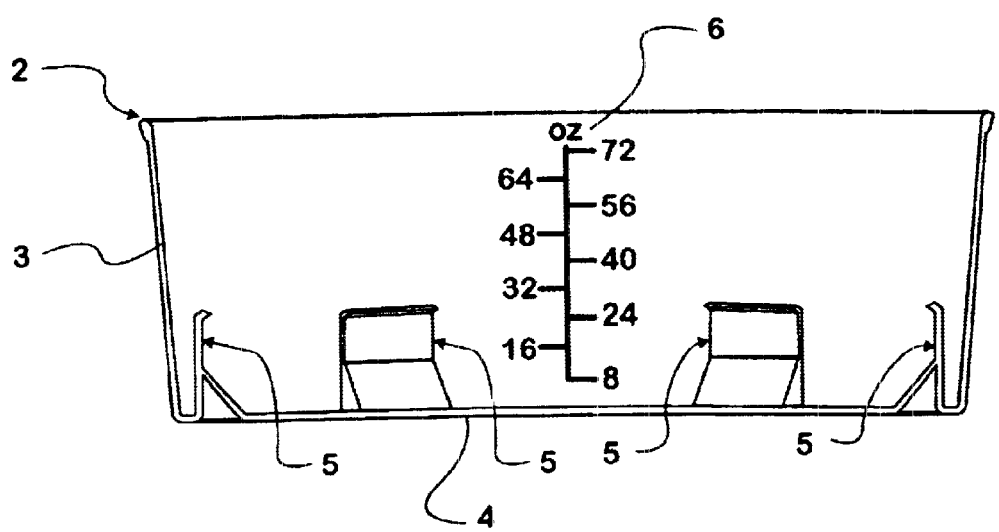
FIG. 2 is a cross-sectional side view showing the interior of the medical bowl according to one embodiment of the invention.

In general and as depicted in FIGS. 1 and 2, the medical bowl 2 of the invention is adapted to accommodate and retain a coiled medical device (not shown in the figures) and comprises a generally smooth cylindrical sidewall portion 3 and a generally planar circular bottom portion 4. The medical bowl 2 is preferably integrally molded and comprises single piece construction. Accordingly, the portions defined as the generally smooth cylindrical sidewall portion 3 and generally planar circular base portion 4 are defined as such in order to afford a distinction relative to the positioning of the retention tabs 5. The bottom portion 4 of the medical bowl 2 further comprises a plurality of retention tabs 5 (illustrated in greater detail in FIG. 5) extending upward from said bottom portion 4 and positioned thereon to provide a gap or space between the sidewall portion 3 and each retention tab 5 as shown, for example, in FIGS. 2 through 5. The juncture of bottom portion 4 and sidewall portion 3, therefore, is not necessarily sharply angled, and can be slightly curved provided it creates a gap or space between the outer side of the retention tab and the interior surface of sidewall portion. The interior surface of the sidewall portion 3 can further comprise markings or indicia, such as volumetric gauge markings 6 as shown in FIGS. 1 and 2.

The overall shape of the medical bowl can be any shape which cooperates with the device intended to be compacted or coiled and placed therein and which permits the retention tabs to function in accordance with the invention. The medical bowl, therefore, can have an overall cylindrical shape. Other suitable shapes include slightly oblong or oval shapes, and the like.

Figure 5:
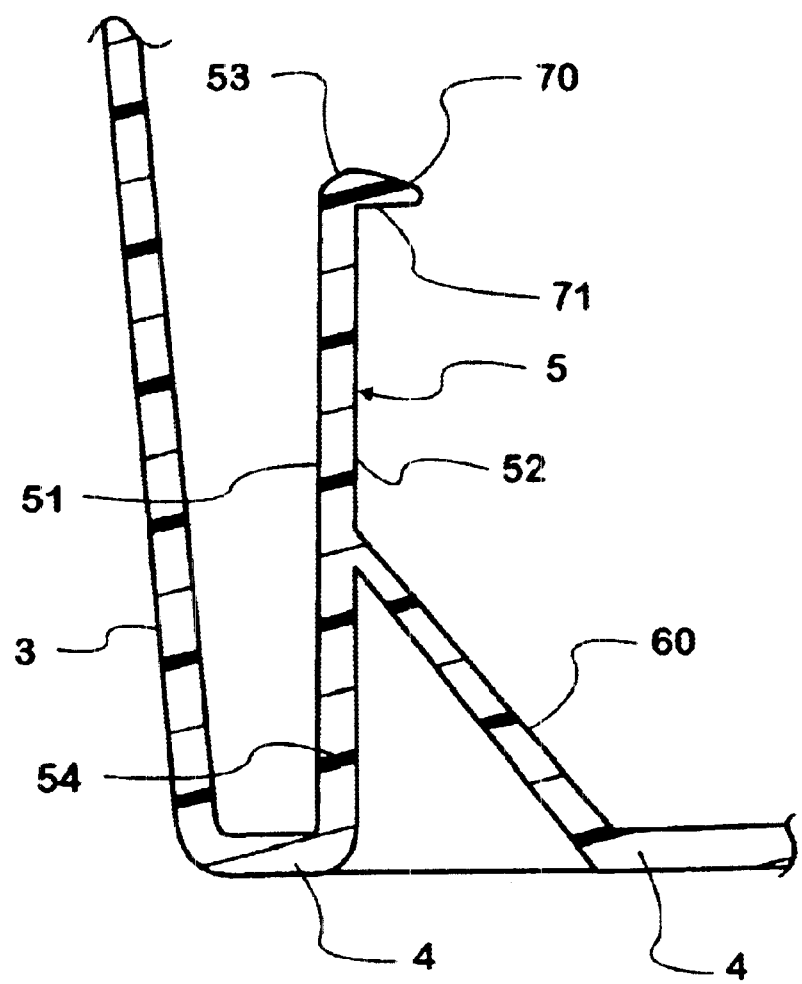
FIG. 5 is a cross-sectional side view of a portion of the medical bowl containing a retention tab according to one embodiment of the invention.

In a preferred embodiment and referring now to FIG. 5, each of the retention tabs 5 comprises an outer side 51, an inner side 52, a top portion 53 and a base 54. The outer side 51 of the retention tab 5 is upright and generally perpendicular relative to the bottom portion 4 of the bowl 2 and generally parallel to said sidewall portion 3. The outer side 51 refers to that portion of the retention tab 5 closest in proximity to the interior surface of the sidewall portion 3 of the bowl 2. The inner side 52 of the retention tab 5 refers to that side of the tab which is positioned closest to the central interior region of the bowl 2. In accordance with the invention, there is a gap or space between the outer side 51 of the retention tab 5 and the interior surface of the sidewall portion 3. This gap or space functions to facilitate the handling and grippability of the coiled device (not shown) when placed within the bowl 2 by providing space to enable the user's finger(s) to be inserted between the coiled device and sidewall portion 3 of the bowl 2 and thereby enhance the manipulation of the coiled device.

Preferably, the inner side 52 of each retention tab 5 comprises an incline portion 60 located at the base 54 and a top portion 53 comprising a lip 70 extending inward toward the central interior region of the bowl 2. The dimensions of the lip 70 can vary in general, but the lip 70 comprises a generally horizontal undersurface 71 so as to effectively control the upward migration of a coiled device when positioned within the bowl 2. The incline portion 60 of the retention tab 5 can comprise a widened solid or hollow portion (as depicted in FIG. 5) of the tab 5 and have an orientation such that the lowermost end of the incline fuses with the bottom portion 4 of the bowl 2 and is positioned closer to the central region of the bowl 2.

The lip 70 and incline portion 60 function cooperatively to retain a coiled device beneath a particular height, i.e., that of the top portion 53 of the retention tab 5, while facilitating the raising of at least part of a coiled device off from full contact with the bottom portion 4 of the bowl 2. The medical bowl of the invention utilizes the tendency of certain resilient coiled devices toward outward expansion in a radial direction to effectuate its retention between the bottom portion 4 of the bowl 2 and the top portion 53 of the tab 5, thereby providing gaps between the coiled device and the bowl surfaces. In addition to separating part of the coiled device from resident fluid which may be present in the bowl, the gap or space also facilitates the handling and grippability of the coiled device inside the bowl by the user.

In a further embodiment, at least a portion of the inner side 52 surface, incline portion 60 surface, or both, of each retention tab can further comprise surface texturing 61 (see FIG. 7) to further control upward migration of a coiled device placed inside the bowl. Suitable surface texturing can include teeth or ridges protruding from the inner side surface, or other friction enhancing means.

The overall dimensions, e.g., height, width and thickness, of the retention tabs 5 can vary. Generally, the retention tabs can have a square or rectangular shape as shown in the Figures. Preferably, the height of each retention tab is less than the height of the sidewall portion of the bowl.

Figure 3:
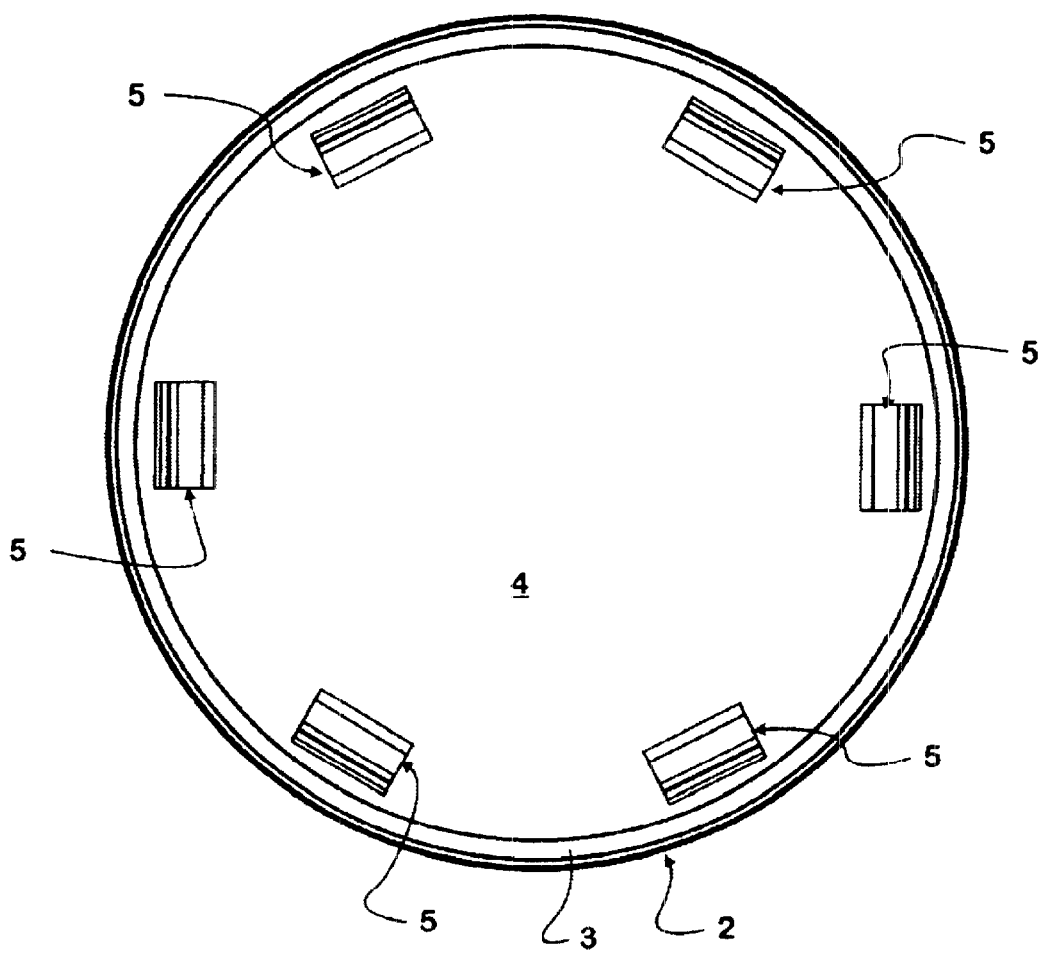
FIG. 3 is a top view of the medical bowl according to one embodiment of the invention.
Figure 4:
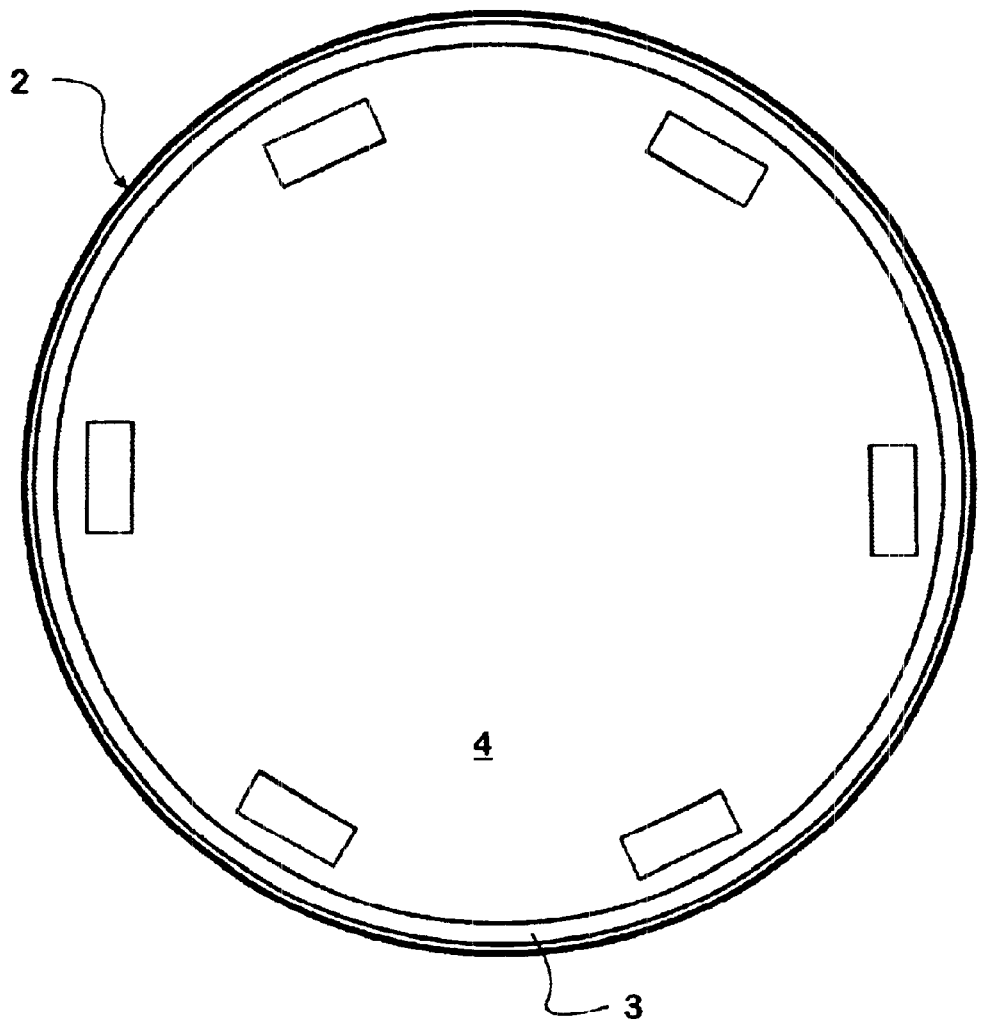
FIG. 4 is a bottom view of the medical bowl according to one embodiment of the invention.

The number of retention tabs can vary provided the number and location of the tabs is sufficient to retain a coiled device inside the bowl. Depending upon the nature of the coiled device, as few as two retention tabs can be used. Preferably, however, the bowl comprises at least three retention tabs. In one embodiment, a total of six, equidistantly-spaced apart retention tabs are on the bottom portion of the bowl as shown in FIGS. 3 and 4.

Figure 6:
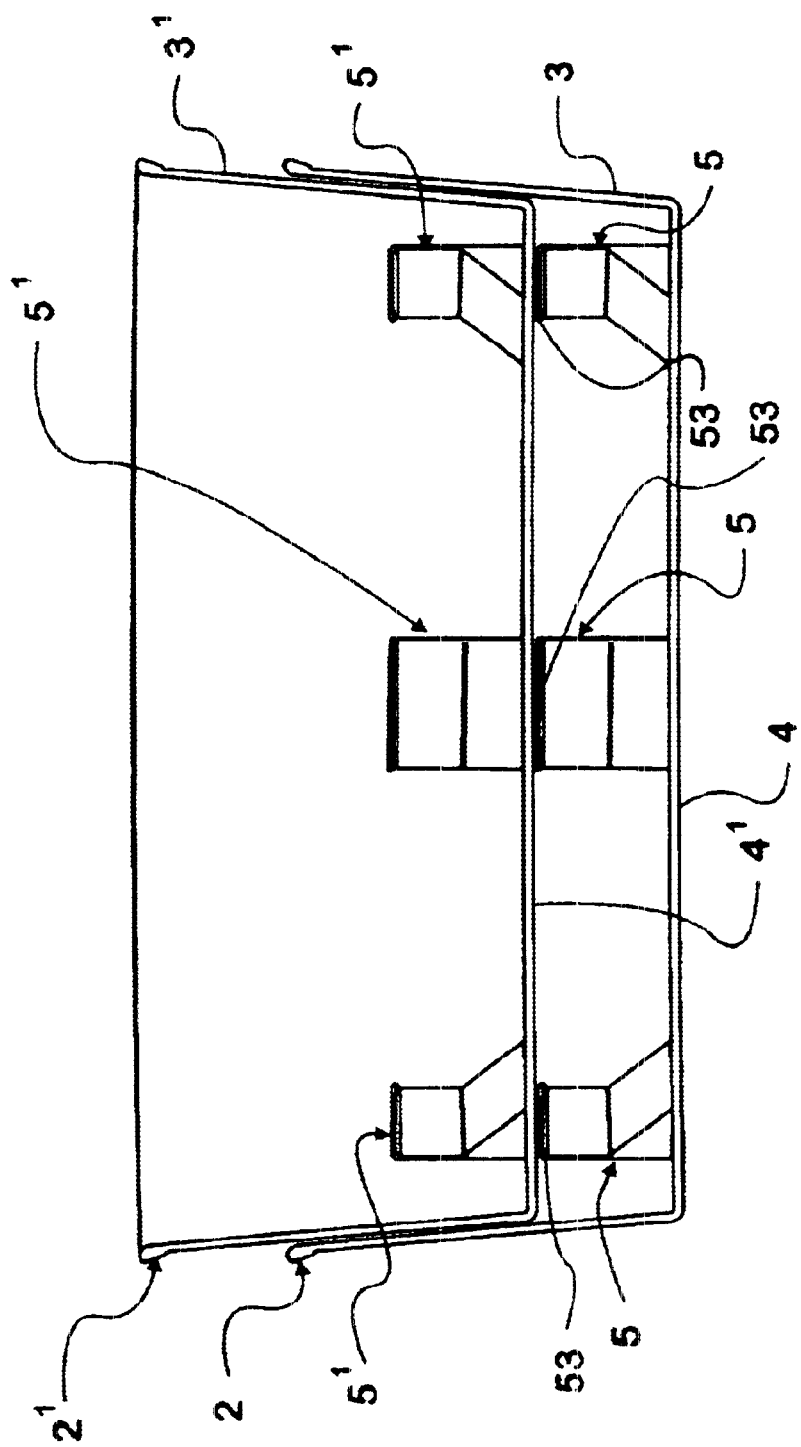
FIG. 6 is a cross-sectional side view of two medical bowls in stacked position according to one embodiment of the invention.

In one embodiment as shown in FIG. 6, the medical bowl 2 of the invention is adapted to be stacked with other such bowls. Accordingly, the interior of a first medical bowl 2 of the invention can be adapted to receive the exterior of a second identical medical bowl (shown in FIG. 6 as 2', the corresponding features of which also contain numerical references indicated by a "'" symbol) such that the top portion 53 of the retaining tabs 5 of the first bowl 2 contact the exterior surface of the bottom portion 4' of the second bowl 2'. Thus, the bowl of the invention can be constructed to be stackable, thereby affording the advantages of space saving with or without a coiled device placed therein. Furthermore, when two or more bowls are stacked as illustrated in FIG. 6, a coiled device can still be retained within the bowl by the retention tabs without being further vertically compressed therein.

In a further embodiment, the bowl of the invention can be adapted to accommodate a lid. When a lid is used, the lid can be constructed to fit over, or seal, the top of the bowl to form a closed container arrangement.

The medical bowl of the invention can be made using conventional molding, machining or processing techniques readily available to those skilled in the art. Examples of suitable molding techniques include, but are not limited to, injection molding, blow molding, rotational molding, and the like. Examples of suitable processing techniques include, but are not limited to, thermoforming, pressure forming, and the like. The medical bowl can comprise an integrally molded single piece construction, and can be composed of plastic or metallic materials suitable for use in the medical field. Preferably, the bowl is composed of a sterilizable polymer.

Figure 7:
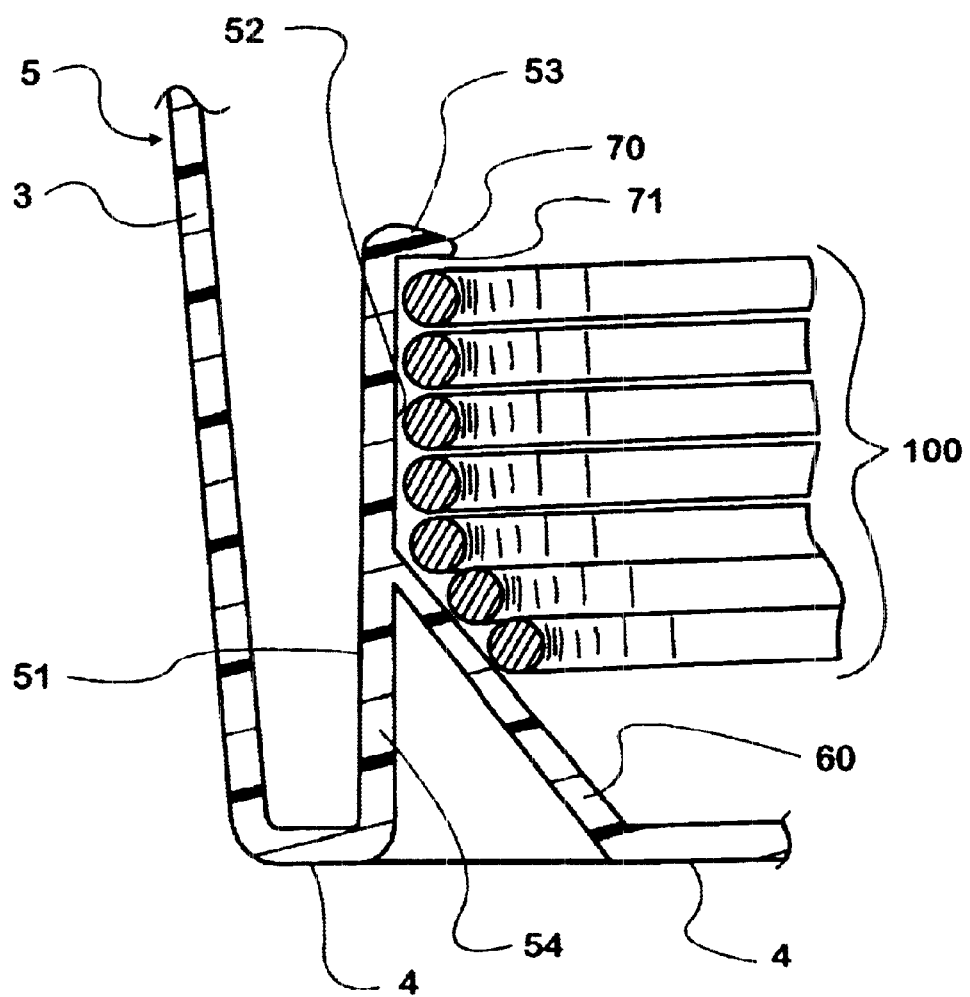
FIG. 7 is a cross-sectional side view of a portion of the medical bowl containing a retention tab and a portion of a coiled device therein according to one embodiment of the invention.

In one example of its use and referring now to FIG. 7, a flexible coiled device 100 (depicted as a guidewire) is compacted on a coiled configuration so as to have a generally diameter smaller than that of the bowl 2 and tabs 5, and placed inside the bowl 2 such that the coiled device 100 resides below the top portion 53 and lip 70 of the tab 5. Upon release of the coiled device 100 by the user's hand, the coiled device 100 expands radially in a slightly uncoiling manner pushing slightly against the inner side 52 of the tab 5, and riding upward along the incline portion 60 of the tab 5. The gap between the tab 5 and the sidewall portion 3 provides a gap circumscribing the coiled device 100 inside the bowl 2 between the tabs 5. Further, the portion of the coiled device 100 at the inclined portion 60 is slightly raised off from the bottom portion 4 of the bowl 2. As a result, the coiled device 100 is "suspended" away from the sidewall 3 and bottom 4 of the bowl thereby facilitating the grasping and manipulating of the coiled device 100 within the bowl 2.

Industrial Applicability

The invention is useful in a variety of applications wherein control over a medical device having a compacted coiled configuration at least at some point during its storage, handling and/or usage, such as guidewires and catheters.

The invention has been described with reference to various and specific preferred embodiments and techniques. It will be understood, however, that reasonable modifications or variations of such embodiments and techniques are possible without departing from the spirit and scope of the invention.

What is claimed is:

1. A medical bowl adapted to accommodate and retain a coiled medical device comprising:
   a generally smooth cylindrical sidewall portion;
   a generally planar circular bottom portion;
   a plurality of discrete retention tabs extending upward from said bottom portion and positioned thereon to provide a space between said sidewall portion and said retention tabs, each retention tab comprising:
      an outer side, inner side, a top portion and a base portion;
      said inner side comprising an incline portion located at the base; and
      said top portion comprising a lip extending inward toward the central region of the bowl;
      wherein said retention tabs facilitate simultaneous and contiguous separation of a retained coiled device from said sidewall portion and said bottom portion of the bowl.

2. The medical bowl according to claim 1, wherein said coiled medical device is selected from the group consisting of a guidewire, catheter, flexible stent, tubing, fiberoptic device, flexible endoscopic device, and wire.

3. The medical bowl according to claim 1 wherein said bowl comprises an integrally molded single piece construction.

4. The medical bowl according to claim 1 wherein said retention tabs extend upward to a height which is less the height of said sidewall portion.

5. The medical bowl according to claim 1 wherein said retention tabs are located at positions between the outer perimeter of said bottom portion and the central region of said bottom portion.

6. The medical bowl according to claim 1 wherein said plurality of retention tabs comprises six equidistantly spaced apart tabs.

7. The medical bowl according to claim 1 wherein each outer side of said retention tabs is upright and generally parallel to said sidewall portion.

8. The medical bowl according to claim 7 wherein the incline portion comprises a lowermost part oriented toward the central region of the bowl.

9. The medical bowl according to claim 8 wherein the exterior surface of the incline portion comprises a textured surface.

10. The medical bowl according to claim 7 wherein said lip comprises a generally horizontal undersurface.

11. The medical bowl according to claim 1 wherein the interior of said bowl is adapted to receive the exterior of a second identical bowl such that the top portion of said retaining tabs of a first bowl contact the exterior surface of the bottom portion of said second bowl in a stackable maimer.

12. A bowl adapted to accommodate and retain a coiled device and having an integrally molded single piece construction, said bowl comprising:
   a generally smooth cylindrical sidewall portion;
   a generally planar circular bottom portion;
   a plurality of discrete retention tabs extending upward from said bottom portion to a height which is less than the height of said sidewall portion and positioned thereon to provide a space between said sidewall portion and said retention tabs, said retention tabs being located at positions between the outer perimeter of said bottom portion and the central region of said bottom portion, each retention tab comprising:
      an outer side, an inner side, a top portion and a base portion; wherein
      said outer side is upright and generally parallel to said sidewall portion;
      said inner side comprises an incline portion located at the base; and
      said top portion comprises a lip extending inward toward the central region of the bowl;
      wherein said retention tabs facilitate simultaneous and contiguous separation of said coiled device from said sidewall portion and said bottom portion of the bowl.

* * * * *